(12) United States Patent
Wetzke

(10) Patent No.: US 11,894,119 B2
(45) Date of Patent: Feb. 6, 2024

(54) LOCATION-INDEPENDENT INGESTION CONTROL

(71) Applicant: Ruma GmbH, Cologne (DE)

(72) Inventor: Monika Wetzke, Leverkusen (DE)

(73) Assignee: Ruma GmbH

(*) Notice: Subject to any disclaimer, the term of this patent is extended or adjusted under 35 U.S.C. 154(b) by 0 days.

(21) Appl. No.: 17/622,250

(22) PCT Filed: Jul. 3, 2020

(86) PCT No.: PCT/EP2020/068899
§ 371 (c)(1),
(2) Date: Dec. 23, 2021

(87) PCT Pub. No.: WO2021/001560
PCT Pub. Date: Jan. 7, 2021

(65) Prior Publication Data
US 2022/0351818 A1  Nov. 3, 2022

(30) Foreign Application Priority Data
Jul. 4, 2019  (WO) ................. PCT/EP2019/067956

(51) Int. Cl.
*G16H 20/13* (2018.01)
*G06V 40/16* (2022.01)
*H04L 9/00* (2022.01)

(52) U.S. Cl.
CPC ........... *G16H 20/13* (2018.01); *G06V 40/172* (2022.01); *H04L 9/50* (2022.05)

(58) Field of Classification Search
CPC ...... G16H 20/10; G06V 40/00; G06V 40/172; H04L 9/00; H04L 9/50
(Continued)

(56) References Cited

U.S. PATENT DOCUMENTS 4,017,616 A  4/1977  Gomez et al.
4,953,562 A  9/1990  Rosen et al.
(Continued)

FOREIGN PATENT DOCUMENTS

DE  10130321 A1  1/2003
DE  10360924 A1  7/2005
(Continued)

OTHER PUBLICATIONS

Khezr, Seyednima et al.; Blockchain Technology in Healthcare: A Comprehensive Review and Directions for Future Research; Applied Sciences 9.9, MDPI AG., Jan. 2019 (Year: 2019).*
(Continued)

*Primary Examiner* — Hiep V Nguyen
(74) *Attorney, Agent, or Firm* — Wolf, Greenfield & Sacks, P.C.

(57) ABSTRACT

The invention relates to a method for monitoring compliance with therapy prescribed by an aP, characterized by the following steps:
  registering the pC in the blockchain (100);
  identifying the exterior packaging by means of a first code (110);
  scanning of the first code by the dispensing point (120);
  linking the patient data to the data of the aP (130);
  starting of an application software by the patient (140);
  scanning the first digital code (150);
  starting the video recording (160);
  ending the video recording (170);
  transmitting the video recording to the aP (180);
  validating the documented ingestion (190).

15 Claims, 2 Drawing Sheets

(58) Field of Classification Search
USPC .......................................................... 705/2
See application file for complete search history.

(56) References Cited

U.S. PATENT DOCUMENTS

| | | | |
|---|---|---|---|
| 5,024,231 | A | 6/1991 | Feldschuh et al. |
| 5,039,616 | A | 8/1991 | Copelan et al. |
| 5,093,265 | A | 3/1992 | Portman et al. |
| 5,179,027 | A | 1/1993 | Fisher et al. |
| 5,206,030 | A | 4/1993 | Wheatley et al. |
| 5,393,054 | A | 2/1995 | Rouffer et al. |
| 5,531,682 | A | 7/1996 | Mazer et al. |
| 5,643,728 | A | 7/1997 | Slater et al. |
| 6,068,981 | A | 5/2000 | Rittenberg et al. |
| 6,303,102 | B1 | 10/2001 | Schlichte et al. |
| 6,440,667 | B1 | 8/2002 | Fodor et al. |
| 7,062,312 | B2 | 6/2006 | Gonzales et al. |
| 7,115,301 | B2 | 10/2006 | Sheu et al. |
| 7,674,625 | B2 | 3/2010 | Gauchel et al. |
| 7,820,444 | B2 | 10/2010 | Keller et al. |
| 7,858,607 | B2 | 12/2010 | Mamchur et al. |
| 7,972,859 | B2 | 7/2011 | Eastwood et al. |
| 8,420,400 | B2 | 4/2013 | Hayward et al. |
| 9,226,874 | B2 | 1/2016 | Siegel et al. |
| 2002/0095072 | A1 | 7/2002 | Gonzales et al. |
| 2004/0037869 | A1 | 2/2004 | Cleverly et al. |
| 2004/0016653 | A1 | 8/2004 | Keller |
| 2005/0008762 | A1 | 1/2005 | Sheu et al. |
| 2006/0029661 | A1 | 2/2006 | Radhakrishnan |
| 2006/0154297 | A1 | 7/2006 | Gauchel |
| 2007/0196927 | A1 | 8/2007 | Gandfils et al. |
| 2007/0298502 | A1 | 12/2007 | Eastwood et al. |
| 2009/0075261 | A1 | 3/2009 | Hayward et al. |
| 2009/0238778 | A1 | 9/2009 | Mordas et al. |
| 2010/0006750 | A1 | 1/2010 | Kolbjorn |
| 2011/0182807 | A1 | 7/2011 | Fuisz et al. |
| 2011/0217243 | A1 | 9/2011 | Siegel |
| 2011/0299081 | A1 | 12/2011 | Manka et al. |
| 2015/0369794 | A1 | 12/2015 | Keller |
| 2018/0374037 | A1* | 12/2018 | Nazzari ............... G09C 5/00 |
| 2019/0035499 | A1 | 1/2019 | Daya |
| 2019/0198144 | A1 | 6/2019 | Blackley et al. |
| 2019/0247174 | A1* | 8/2019 | Zegarelli ............. A61C 19/063 |
| 2020/0309763 | A1 | 10/2020 | Keller et al. |

FOREIGN PATENT DOCUMENTS

| | | | | |
|---|---|---|---|---|
| DE | 10112470 | B4 | 2/2008 | |
| DE | 102017220500 | A1 | 5/2019 | |
| EP | 1410014 | A1 * | 4/2004 | ........... G01N 33/483 |
| EP | 1410014 | A1 | 4/2004 | |
| EP | 1462118 | A1 | 9/2004 | |
| EP | 1563311 | A1 | 8/2005 | |
| EP | 2502621 | A1 | 9/2012 | |
| EP | 2957909 | A1 * | 12/2015 | ........... G01N 33/493 |
| GB | 2271848 | A | 4/1994 | |
| GB | 2320960 | A | 7/1998 | |
| JP | 2000-028614 | A | 1/2000 | |
| WO | WO 1998/012557 | A1 | 3/1998 | |
| WO | WO 1998/014275 | A1 | 4/1998 | |
| WO | WO 1998/036775 | A1 | 7/1998 | |
| WO | WO 1998/018003 | A1 | 4/1999 | |
| WO | WO 1999/017747 | A1 | 4/1999 | |
| WO | WO 1999/056789 | A1 | 11/1999 | |
| WO | WO 2000/074781 | A1 | 12/2000 | |
| WO | WO 2002/056919 | A2 | 7/2002 | |
| WO | 02075307 | A1 | 9/2002 | |
| WO | WO 2004/046715 | A2 | 6/2004 | |
| WO | WO 2007/095622 | A2 | 8/2007 | |
| WO | WO 2009/136763 | A1 | 11/2009 | |
| WO | WO 2011/032584 | A1 | 3/2011 | |
| WO | WO 2011/091413 | A1 | 7/2011 | |
| WO | WO 2013/078403 | A1 | 5/2013 | |
| WO | WO 2014/058582 | A1 | 4/2014 | |
| WO | WO 2014/210434 | A1 | 12/2014 | |
| WO | 2018037148 | A1 | 3/2018 | |

OTHER PUBLICATIONS

International Search and Written Opinion for App. No. PCT/EP2019/067956 dated Mar. 2, 2020.
International Search and Written Opinion for App. No. PCT/EP2020/068899 dated Aug. 10, 2020.
Opposition of EP 02732486: "Communication of a notice of opposition" dated Sep. 27, 2007.
Opposition of EP 02732486: "response to the Opposition" dated Dec. 18, 2007.
Opposition of EP 02732486: "Summons to attend oral proceedings" dated Aug. 19, 2010.
Opposition of EP 02732486: "Brief Communication" dated Sep. 20, 2010.
Opposition of EP 02732486: "Second Reply to the Summons to Attend Oral Proceedings" dated Sep. 20, 2010.
Opposition of EP 02732486: "Minutes of the oral proceedings before the Opposition Division" dated Oct. 20, 2010.
Opposition of EP 02732486: "Interlocutory decision in Opposition proceedings" dated Apr. 14, 2011.
Opposition of EP 02 732486: "Acknowledgement of receipt of the document specified above" dated Apr. 14, 2011.
Opposition of EP 02732486: "Decision to maintain the European patent in amended form" dated May 18, 2012.
Bjarnason et al., Comparison of four markers of intestinal permeability in control subjects and patients with coeliac disease. Scand J Gastroenterol. Jul. 1994;29(7):630-9. doi: 10.3109/00365529409092484.
Bjarnason et al., I, Intestinal permeability: an overview. Gastroenterology. May 1995;108(5):1566-81. doi: 10.1016/0016-5085(95)90708-4.
Donovan et al. Absorption of polyethylene glycols 600 through 2000: the molecular weight dependence of gastrointestinal and nasal absorption. Pharm Res. Aug. 1990;7(8):863-8. doi: 10.1023/a:1015921101465.
Eaton et al., Gut permeability measured by polyethylene glycol absorption in abnormal gut fermentation as compared with food intolerance. J R Soc Med. Feb. 1995;88(2):63-6.
Miki et al., Rapid and simultaneous quantification of rhamnose, mannitol, and lactulose in urine by HPLC for estimating intestinal permeability in pediatric practice. Clin Chem. Jan. 1996;42(1):71-5.
Philipsen et al., Gastrointestinal permeability to polyethylene glycol: an evaluation of urinary recovery of an oral load of polyethylene glycol as a parameter of intestinal permeability in man. Eur J Clin Invest. Apr. 1988; 18(2):139-45. doi: 10.1111/j.1365-2362.1988.tb02404.x.
Ukabam et al., Small intestinal permeability to mannitol, lactulose, and polyethylene glycol 400 in celiac disease. Dig Dis Sci. Sep. 1984;29(9):809-16. doi: 10.1007/BF01318423.
Young et al., Measurement of polyethylene glycol 400 in urine by direct-injection high-performance liquid chromatography. Clin Chem. Oct. 1990;36(10):1800-2.
Thatcher Camden et al. "Pharmaceutical uses of Blockchain Technology", 2018 IEEE International Conference on Advanced Networks and Telecommunications Systems (ANTS), IEEE, Dec. 16, 2018, pp. 1-6.

* cited by examiner

LOCATION-INDEPENDENT INGESTION CONTROL

The invention relates to the field of health care.

More particularly, the invention relates to controlling the ingestion of a particular pharmaceutical composition.

CN108538355 A describes a device and method for assurance that a patient has taken the drug. The drug intake assurance device comprises a video capture device, a storage device, and a processing device. The video capture device is configured to store one or several video sequences. The processing device may analyse the video sequences to determine suspicious activities of the user. The processing device is configured to detect matching drug packages.

DE 10 2014 007249 A1 describes a device that can be used for person recognition, reminder, and/or timing of administration deadlines. The device also enables the user to check the drug intake and whether the user has excreted the drug by vomiting.

The present invention proposes a method for tracing the path of a pharmaceutical composition from manufacture to patient ingestion.

DEFINITIONS

Pharmaceutical Composition (PC)

A pharmaceutical composition (PC) within the meaning of the invention is a composition that is administered to a patient as part of a therapeutic treatment, or as part of a diagnostic procedure. A PC may, therefore, contain active substances for the treatment of illnesses. However, the PC may also contain only substances that cannot be metabolised to authenticate the patient's biological samples and no active substances. However, the PC may contain both an active substance and substances that cannot be metabolised to authenticate the patient's biological samples.

The PC may be suitable for any form of administration, such as oral, parenteral, enteral, or percutaneous use. The PC may be in any form, such as a powder, solution, tablet, capsule, or pre-filled syringe.

PC refers to a generic pharmaceutical composition that has a defined composition. An individual PC designates an individually packaged PC.

Container

A container within the meaning of the invention is an article in which the PC is contained.

The container may be any type of enclosure that directly encloses the PC. For example, the container may be a vial, blister pack, syringe, bag, or the like.

Outer Packaging

The container according to the invention is in an outer packaging.

The outer packaging contains the container according to the invention and possibly also further information, such as instructions for use or package inserts.

The First Code

The first code is a digital code printed on the outer packaging and identifies the PC.

The Second Code

The second code is a digital code printed on the container.

Authorised Persons (AP)

Authorised persons (AP) according to the invention are persons authorised to issue the PC to the patient, to send it to the patient, or to review the treatment goals and results. AP may also be individuals who validate the taking of the PC in the captured video. The AP are, e.g., doctors, medical practitioners, pharmacists, hospital staff, probation officers, artificial intelligences (AI), etc.

Application Software

Application software is a computer program stored on an electronic device and is used to process and support desired function. This computer program may also be configured and offered in the form of application software for mobile electronic devices ("app" or "mobile app"). According to the invention, the application software supports capturing a video of the patient and forwarding of such captured videos to the predetermined digital address via a blockchain. The application software may also have some other features, such as time-limited video capture, facial recognition, digital code recognition, etc.

Adherence

According to Wikipedia (https://de.wikipedia.org/wiki/Adhärenz), the term of adherence describes the extent to which a person's behaviour, such as drug intake, a diet regime, or a lifestyle change, is consistent with recommendations agreed with the therapist. The basis of successful therapy—according to this view—is consideration of the individual needs of the patient as well as consideration of factors that make it difficult for the patient to achieve the therapy goal. Good adherence corresponds to consistent adherence to the treatment plan agreed with the therapist.

According to the World Health Organisation (WHO), only 50% of all patients on average achieve good adherence. Adherence is particularly important in chronically ill patients, for example regarding intake of drugs, following a diet, or changing lifestyle. The term of compliance is used synonymous with adherence below.

Blockchain

The blockchain links the data records involved ("blocks") to create a coherent chain of information. Within the blockchain, each block is linked to the block before and after it, creating an irreversible, unalterable chain.

Linking of the blocks prevents a block from being changed or another block from being inserted between two existing blocks.

Each block typically contains a cryptographically secure hash (scatter value) of the previous block, a timestamp and transaction data (see https://de.wikipedia.org/wiki/Blockchain)

The blockchain can be used in any application. It is critical for the blockchain that later transactions and the blocks based on them are built on previous transactions and validate them as correct by proving knowledge of the earlier transactions. This renders it impossible to manipulate or erase the existence or content of the earlier transactions without also destroying all later transactions. The use of a blockchain permits decentralised accounting for the transactions. Other participants in the decentralised ledger who still have knowledge of subsequent transactions would recognise a tampered copy of the blockchain by the fact that it has inconsistencies in its calculations, such as hash calculations.

A blockchain makes it possible, for example, to reach a consensus between the nodes of a decentralised network on creation of an additional block that is added or appended to the blockchain. For example, the consensus procedure may be based on a proof-of-work or a proof-of-stake.

In accordance with the invention, blockchain technology is used to store and verify the path of a PC from manufacture to the point of dispensing, to the patient, and the verifiable ingestion of the PC by the patient in a tamper-proof manner.

Electronic Device

An electronic device is as a device that is functionally suitable for use of the application software according to the invention and that is used for voice and data communication.

For example, an electronic device comprises a memory that stores program instructions, such as program instructions of the application software, and a processor configured to execute the program instructions and control the electronic device according to the program instructions. The electronic device further comprises a camera configured, for example, to record the administration of the PC and/or to scan codes. The electronic device further comprises, for example, input and output devices for inputting and outputting data. The electronic device further comprises, for example, a communication interface for communicating via a network, such as the internet.

Digital Twin

According to the Gabler business dictionary, a digital twin is a virtual model, e.g. of a process, a product, or a service, that connects the real and virtual worlds.

This coupling of the virtual and real worlds enables the analysis of data and the monitoring of systems, so that the entire life cycle of a product can be created.

According to the invention, a digital twin can be used to replicate the PC.

FIELD OF THE INVENTION

The method according to the invention can be used in the entire field of medicine for both chronic and acute illness. A complete log of when the patient has taken what or when what was administered to the patient can be kept using the method according to the invention, in particular regarding which PC was taken/administered when. This enables the AP who prescribed the PC, as well as the health care systems, to verify that the PC is being taken as prescribed, if necessary also down to the individual dose.

The PC may contain an active substance, so that the method according to the invention may be used to improve patient adherence.

However, the present invention can also be used in the context of endogenous marking of urine samples. This is done in particular for detection of substance abuse. Potential areas of application include substitution treatment for opiate addicts, drug therapy, doping control, and abstinence control. Two exemplary aspects are of particular importance in substitution treatment:

on the one hand, it must be ensured that the patient actually takes the substitution substance and does not feign taking it in order to sell the substitution substance, if necessary, and on the other hand, dangerous co-use must be excluded, which is usually done by urine analysis.

BRIEF DESCRIPTION OF THE FIGURES

The present invention makes it possible to keep a complete log from the time of manufacture to the time of ingestion of a PC. This logging takes place in a blockchain where all relevant actions of the parties involved in the process regarding these PC are registered.

A schematic representation of the invention is shown in FIG. 1.

Figure 2:
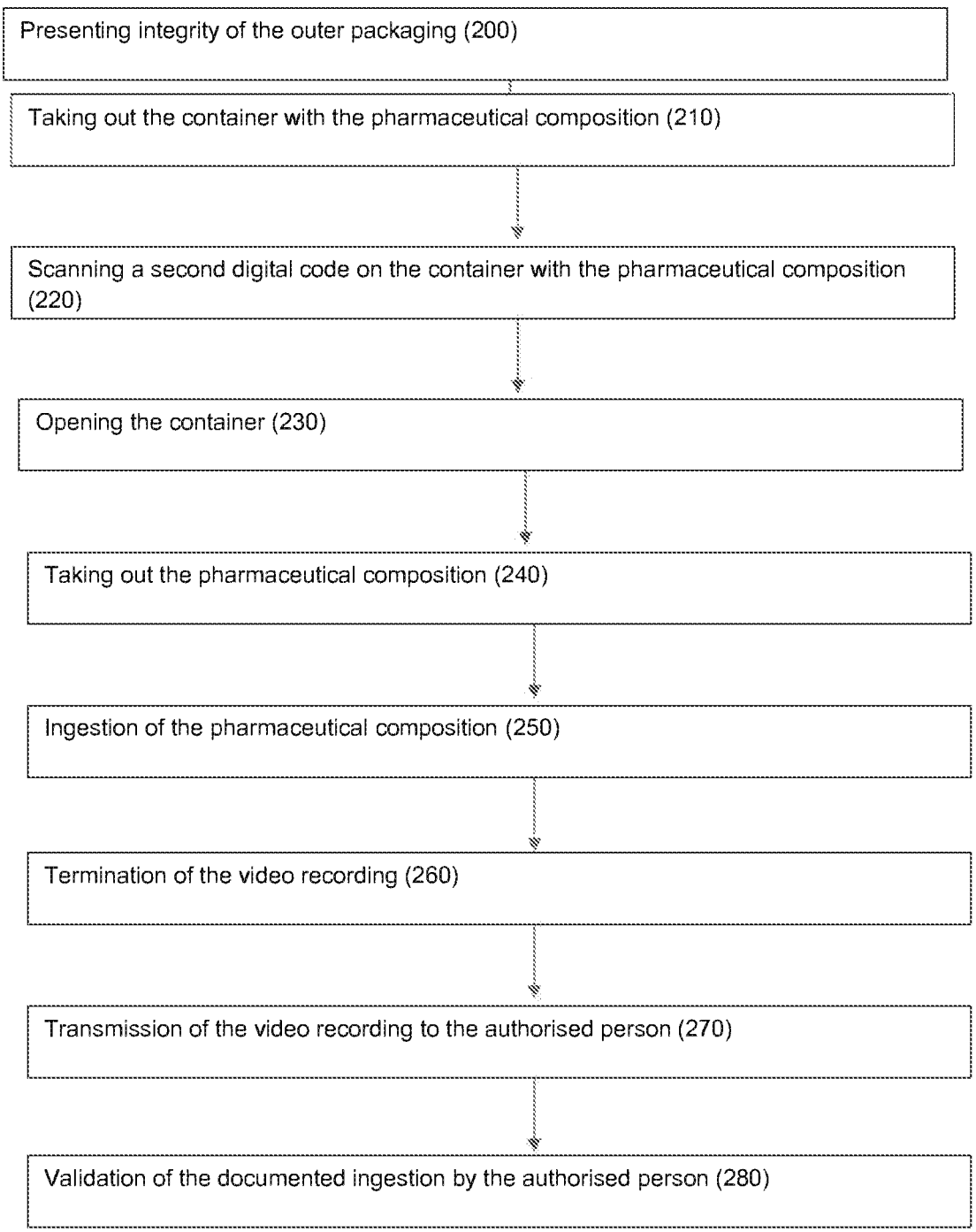

An illustration of the invention in endogenous marking of urine samples is shown in FIG. 2.

DETAILED DESCRIPTION OF THE INVENTION

The securPharm system connected to the EU Hub is used in Germany, for example, to ensure protection against counterfeiting. This system is based on the end to end principle, where the two ends of the logistics chain serve to provide security (see https://www.securpharm.de/sicherheitsmerkmale/). One end is the pharmaceutical provider (PP) that places a PC on the market. The other end is the dispensary, such as a public pharmacy.

Regulation (EU) 2016/161 (Anti-Counterfeiting Directive) requires two security features on the package of prescription drugs for human use:

An anti-tampering device that can be used to detect whether the outer packaging of a medicinal product is intact. This security feature must be implemented by each pharmaceutical provider separately. DIN EN 16679 provides a uniform European standard for this.

An individual identification feature (unique identifier) that renders every package unique and uniquely identifiable via the digital product code it contains. This unique identifier is the basis for the authenticity check by the securPharm system.

The pharmaceutical provider applies the security features to each package during the production process. The data of the unique identifier (serial number, product code, batch number, expiry date) are applied to the package in plain text and in the data matrix code and uploaded to the central database of the pharmaceutical industry. The data matrix code is scanned before dispensing to the patient to verify its authenticity. This compares the data in the package with the data in the system. The status of the package is reported back to the pharmacy, i.e. whether the unique identifier has been activated or already deactivated. In the latter case, the package must not be given to the patient.

The invention has the task of not only verifying the manufacturer and dispensary, but also making it possible to trace the entire chain from production of the PC to intake by the patient.

The invention is explained in more detail with reference to FIG. 1.

Figure 1:
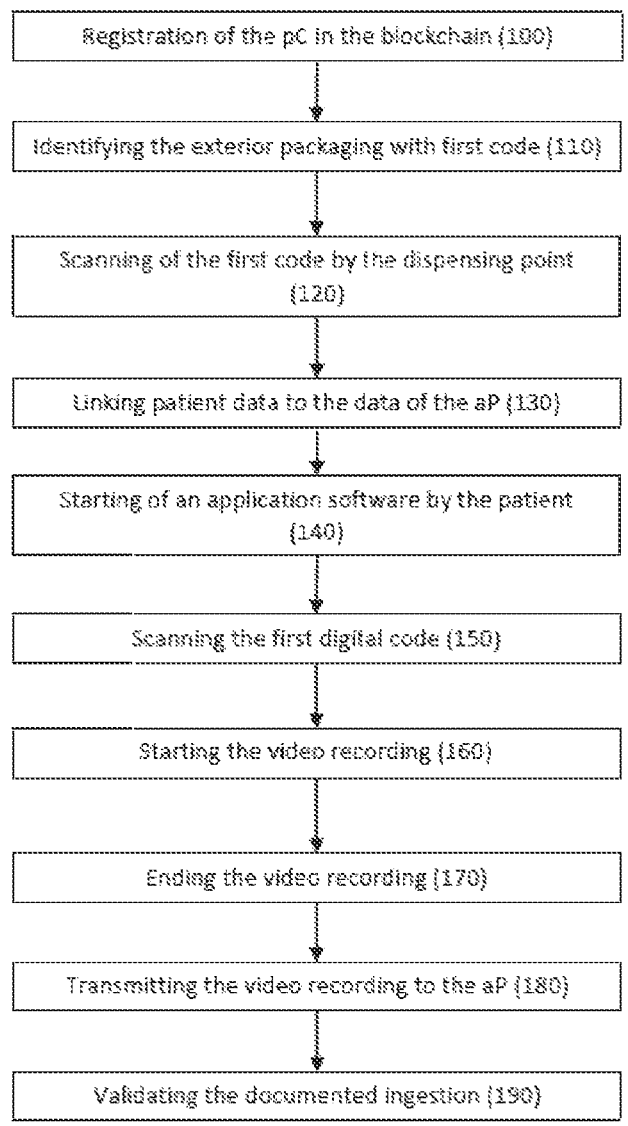

For example, FIG. 1 shows the steps taken from manufacture to validation of ingestion.

Registering the PC in the blockchain (100);
Marking the outer packaging with a first code (110);
Scanning the first code from the dispensary (120);
Linking patient data with AP data (130);

Starting an application software by the patient (140);
Scanning the first digital code (140);
Starting the video capture (150);
Stopping the video capture (160);
Transmitting of the captured video to the AP (180);
Validating the documented intake (190).

In step 100 of FIG. 1, the PC in the blockchain is registered within the scope of the manufacturing process. This is possible, for example, using digital twins.

In step 110 of FIG. 1, the outer packaging of the PC is marked with a first digital code by the manufacturer. According to the securPharm system, the data of the first code (serial number, product code, batch number, expiry date) are applied to the outer packaging in plain text and in the digital code.

In step 120, the code is scanned to verify authenticity prior to dispensing to the patient. The dispensary can be the pharmacy or the AP.

In step 130, the patient data can be linked to the AP data by scanning the first code. This link can be created automatically by scanning the first code, or manually by the AP. The captured video of the patient taken at step 160 can be sent to the correct digital address of the AP at step 130 by linking the data.

The time at or period in which the patient is to take the PC can be determined by the AP.

The invention also envisages that the patient receives an electronic message before the specified time, either instructing the patient when to take the drug or reminding the patient to take the drug. The electronic message can be, for example, an email, a text message, or a push message.

The patient starts an application software (step 140) installed on an electronic device before taking the PC. The electronic device can be stationary (computer or computer terminal) or mobile (e.g. mobile phone, tablet, or laptop).

The patient can start the video capture in the application software (160) to prove that the PC has been taken after the patient scans (150) the first digital code on the outer packaging.

Encrypted or unencrypted data transmission can be activated automatically by starting the application software.

For evidence of patient ingestion of the PC, the video capture includes one or several of the following actions: showing the patient's face, showing the patient opening the outer packaging, showing the patient removing the container from the outer packaging, showing the patient removing the PC from the container, or showing the patient ingesting the PC. After the video capture is completed (170), this captured video is then sent to the AP for validation (190) in step 180. After validation, specific information can be made available to health systems for settlement purposes.

The captured videos can be validated by an AI or AP. The AI may then have facial recognition software.

A further object of the invention is ensuring that every individual PC can be tracked as a single dose from manufacture to administration or ingestion. This is to ensure on the one hand that authenticity of the PC is ensured and on the other hand that the patient to whom the respective PC has been prescribed has actually taken it. For this purpose, a second code is applied to the container that holds the individual PC. This means that a code is assigned to every individual PC. The PC must, therefore, be enclosed individually. The enclosure of the PC is applied with a code. However, it is also possible that several PC are packed together, e.g. in a blister pack. However, it must be ensured that a unique code is assigned to each PC in this case.

This embodiment is particularly advantageous when the AP is concerned that the patient does not intend to take the PC. This behaviour is often observed in substance abuse and endogenous marking of urine samples.

In substance-abuse testing, it is very important to avoid any possibility of tampering with a urine sample. Urine markers are used for this purpose. The outer packaging of the urine markers for secured urine testing is designed in such a way that several tamper-evident features are effective during the opening process. The application software requires proof of these tamper-proof features at defined process steps during the collection of the urine marker for assurance of clear allocation of the urine to the patient. If such proof is not provided, the current session will be terminated automatically, and the session fragment will be forwarded to the AP for validation.

This approach can be synchronous, i.e. with simultaneous communication between patient and AP within the scope of a virtual consultation, or asynchronous, i.e. at different times, so that the recording takes place at a different time than the validation of the video capture by the AP. This makes it possible to ensure that the PC can be taken at any time and location-independently, and that manipulation of the PC is impossible.

For example, therapy success is determined by urine testing in substitution therapy of drug addicts. The effort of concealing any return to substance abuse out of fear of sanctions is, therefore, to be expected.

In the context of such a substitution therapy, the PC for urine authentication by chromatographic analysis used in the method according to the invention does not contain any active substance, but a combination of the marker substances that generally cannot be metabolised; this is to prevent falsification of the urine samples. If the marker substance is not taken reliably, it can be given to another person who does not take any drugs at a later date and their urine can be submitted for testing. The method of using markers and in particular polyethylene glycols of different molecular weights to prevent the tampering of urine samples is described in EP 1 410 014. Use of capsules containing the marker substances is described in EP 2 957 909.

In another embodiment, the PC used in the substitution therapy may contain the active substance.

The task of the invention is solved in that every individual dose of a PC is registered in a blockchain during its production and subsequent packaging.

The PC are dispatched to laboratories that in turn can supply facilities of the AP, at endogenous marking of the urine samples in one embodiment. In another embodiment, the AP are supplied directly. Patients receive the PC directly from the AP. Normally, the AP does not know the composition of the marker substances. The blockchain links the entities involved to create a coherent chain of information. This enables the laboratory to verify the identity of the PC.

When using the method according to the invention in endogenous urine sample marking, e.g. in substitution therapy, the patient must ingest the PC by following precisely defined steps that ensure that the marker combination has actually been ingested by the patient who provides the urine sample. In a first step, the PC in the container is removed from the outer packaging and the first code located on the outer packaging is scanned with the electronic device. However, the first code can also be scanned before the container is removed with the PC. Next follows the step of scanning a second digital code located on the container containing the PC.

The video capture can commence automatically by scanning the second code. Alternatively, the user may be given time to sit down, and/or to secure the electronic device, e.g. in a holder, after scanning the second code. Then the user would have to start the video capture actively, e.g. by pushing a button or key on the physical or on the display of the electronic device.

The following steps, which are recorded in the video capture, can be provided after starting the video capture and before taking the PC:

Opening the container;
Removing the PC;
Taking the PC;
After this, the video capture is ended, transmitted to the AP, and finally validated.

A time window starts at commencement of the video capture. This means that the video capture must start in a period of time during which the steps of the method according to the invention must be performed. This is meant to prevent manipulations. The AP will be informed if the intake does not occur during this time window. There may be a provision that the video capture cannot be repeated with the same PC. In such a case the patient must make a new appointment with the AP.

In one embodiment, the time window is up to 120 sec. In another embodiment, the time window is 30, 45, 60, 75, 90, or 120 sec.

There may be another removable code on the container that is used to identify the urine sample before shipment to the laboratory.

In particular in the case of endogenous marking of the urine sample, the ingestion of products may only be pretended in order to pass them on at a later date. In this case, a dye can be added to the PC to colour the oral mucosa, provided that the PC is not swallowed but remains in the mouth for a certain time.

If desired, therefore, another step may be provided in the method according to the invention, in particular that of checking the oral cavity following ingestion.

In one embodiment, the first code is a one-dimensional code or a multi-dimensional code.

In another embodiment, the second code is a two-dimensional code.

In another embodiment, the first code and the second code are two-dimensional codes.

In another embodiment, the two-dimensional codes are QR codes.

The method according to the invention can be used for various purposes.

It can be used, for example, to increase patient adherence to a particular treatment and thereby improve treatment success.

However, the application software may also be provided to AP by the health system for settlement purposes. This may enable patients who demonstrate good adherence to receive a discounted invoice, for example.

Furthermore, the method according to the invention can be used in the endogenous marking of the urine sample to verify the location-independent ingestion of the marker substances. This may be used to ensure that the urine sample is from the specific patient without the need to order the patient into the office.

The invention further comprises application software stored on a computer-readable medium that enables a processor to scan a first code on the outer packaging of a PC, receive data from a blockchain, capture the video, and transmit the video capture to the blockchain. The application software is configured to interface with the blockchain.

The application software is preferably stored on a mobile device. The mobile terminal is preferably a mobile phone or smartphone, a tablet, or a laptop.

For example, management of the PC or a digital twin of the PC in the blockchain is performed by an intermediary or management entity. For example, the management entity uses a dedicated digital identity to interact with the blockchain. This identity is used to manage the PC in the blockchain and to forward data records generated by users of the application software to the blockchain for registration as a transaction. For example, the management entity thus bears the costs of these transactions. The management entity may charge these costs to the users of the application software. For example, the management entity will provide the application software. In some embodiments, the digital identity comprises, for example, an asymmetric cryptographic key pair associated with the management entity, comprising a private cryptographic key (private key) and a public cryptographic key (public key). Creation of the corresponding digital identity can, for example, take place on any computer system of the management entity, or also completely offline. For example, before initial use in a transaction, the corresponding identity is initially unknown to the blockchain. For example, the public cryptographic key is used to generate an address, such as using a hash function, as the origin or destination address for transactions in the blockchain. The private key, for example, is used to generate a credential, such as a signature, for a transaction from an originating address based on the associated public cryptographic key.

In some embodiments, the management entity generates a digital twin for a PC comprising a unique identity or identifier of the PC. For example, two additional cryptographic keys are generated for each PC: A first key A and a second key B. In some embodiments, the keys A and B may each be merely a random string of characters; for example, key A comprises 32 characters, e.g. lower-case letters, upper-case letters, and/or numbers. Like the identifier of the PC, key A is unique and can uniquely identify the PC. For example, key B comprises 8 characters, e.g. lower-case letters, upper-case letters, and/or numbers. Key B, for example, is not unique in itself, but assigned to the same PC and serves, for example, as a check value to determine whether the PC container matches the outer packaging. In the blockchain a PC is identified its key A, for example. For example, the identity of the PC is information that is stored for this PC.

For example, the management entity generates the digital twin of the PC using a data contract or smart contract within a digital twin of the management entity or associated with a digital twin of the management entity. The corresponding generation is documented, for example, in a data record that is transmitted to the blockchain for registration as a transaction.

For example, the AP is a doctor in a doctor's practice. Practice application software or practice app is run on a computer system in the doctor's practice. For example, in order for a doctor to be able to use the practice app and its functions, they need a unique identity they can use to execute or initiate transactions in the blockchain. In some embodiments, the doctor generates an identity.

For example, the practice app enables the user to choose whether the user is a doctor or an employee of the practice upon launching. For the purpose of the following embodiments, the user is assumed to be a doctor. Subsequently, the case of use by an employee will be considered.

For example, when starting the practice app, the doctor chooses to use it in their capacity as a doctor. For example, the practice app provides the doctor with the ability to create a personal identity. For example, this identity may comprise random information, such as comprising a random string of characters or a sequence of random words. The doctor must keep this random information safe, for example, by writing it down, For example, this random information represents a private cryptographic key associated with the doctor or information from which the doctor's private cryptographic key can be derived. This private key, and as a result the random information, must be kept secret, as there is a risk that someone else may impersonate the doctor and misuse the practice app otherwise.

In some embodiments, the doctor additionally assigns a password; this may be, for example, simpler, i.e. shorter, than the random information. This password is used to protect the random information against foreign and/or unauthorised access in a simpler and more effective way. For example, the identity is created locally on a computer of the doctor on which they execute the practice app.

For example, once the doctor has created their identity, the doctor can further create a digital twin of the doctor's practice in the blockchain. The doctor first generates a digital twin of the doctor's practice for this. For example, a data record to generate the digital twin of the doctor's practice is sent from the doctor's computer to an API of the management entity via an HTTP request.

An API ("Application Programming Interface") refers to a programming interface, i.e. a program part made available by a software to other programs for connection to the software or to the system provided by the software. This program binding is provided at source code level, for example.

For example, the management system generates another transaction on behalf of the doctor and submits it to the blockchain. In some embodiments, the doctor's data are encrypted. Since the doctor's data are encrypted, the management system API does not have any access to them. Transfer of the data or data record for registration as a transaction by the API of the management system takes place, for example, so that the costs for execution of the corresponding transaction can be borne by the management system.

For example, the following data areas are assigned to the digital twin of the doctor's practice: Patients, their information, and reference to their identity; PCs dispensed or prescribed by the practice and their progress information; the practice's employees and their linked identities; and/or an area for validation results of the administration of the PCs. For example, the area for the validation results of the administration of the PCs is a separate area for data protection reasons.

In some embodiments, the doctor may further create and generate digital identities for employees of the practice using the practice app. The practice employees need these dedicated identities, for example, so that the doctor can transfer administrative tasks to the corresponding employees. The corresponding identities of the employees are assigned, for example, access rights to data within the doctor's practice that enable the corresponding employee, for example, to make changes to this data in their own name.

For example, the doctor generates an additional identity for the employee that comprises an asymmetric cryptographic key pair associated with the employee. A public cryptographic key of the employee's asymmetric cryptographic key pair and an identifier of the employee, such as a name of the employee entered by the doctor, are entered into an employee data record of the digital twin of the practice. For this purpose, for example, a data record is generated to register the employee and transmitted to the API of the management entity, which signs the data record and forwards it to the blockchain for registration as a transaction.

For example, after the employee is registered using the transaction, a private cryptographic key of the employee's asymmetric cryptographic key pair is provided to the doctor. For example, the employee's private cryptographic key is displayed to the doctor in the form of a QR code that comprises the corresponding private cryptographic key. This QR code can be used by the employee to set up and use the corresponding employee identity on another electronic device. The QR code is scanned with the other device for this, for example.

In some embodiments, the doctor may further edit the data of the registered employee. The doctor will edit the employee data record using the practice app to change the employee's data. A record comprising the corresponding changes is created and submitted to the API of the management entity by the doctor. The management entity forwards the data record to the blockchain for registration as a transaction.

In some embodiments, the doctor may also delete a registered employee using the practice app. A data record that comprises information on the following operations is generated for this purpose: The employee's identity is removed from a list of registered employees of the doctor's practice, access rights to the practice's data assigned to the corresponding employee identity are removed, and the corresponding data for which the employee identity had access rights is re-encrypted to ensure that the employee whose identity was deleted is no longer able to decrypt the corresponding data afterwards. This record is sent to the API of the management entity, which forwards the data record to the blockchain for registration as a transaction.

In some embodiments, the practice app enables, for example, the doctor or an employee of the practice, to create or register patients in the practice app. For this purpose, an identity is generated for the patient, comprising an asymmetric cryptographic key pair associated with the patient. Further, a patient data record is generated for the digital twin of the doctor practice, comprising a public cryptographic key of the patient's asymmetric cryptographic key pair, a patient identifier, and a photograph of the patient, if applicable. Information for creating the patient data record is submitted by the doctor or employee as a data record to the API of the management entity that forwards this data record to the blockchain for entry as a transaction.

Once the patient has registered, a private cryptographic key of the patient's asymmetric cryptographic key pair is provided to the patient, for example in the form of a QR code comprising the private cryptographic key for coupling the patient app. The patient can use this private cryptographic key later for documenting the administration of the PC.

In some embodiments, the practice app allows the doctor and/or an employee of the practice to process the data of registered patients. For example, the doctor or employee changes the patient's name or photo and generates a data record to log the change. The corresponding data record is transmitted to the API of the management entity and forwarded by it to the blockchain for registration as a transaction.

In some embodiments, the practice app provides doctor or employee the ability to archive a patient. An archived patient no longer appears on a list of active patients and is blocked from dispensing or administration of the PC. For example, the doctor or employee will move the patient's identity from the list of active patients to a list of archived patients within the digital twin of the doctor's practice and remove all patient access rights to originally linked PCs. These changes are documented in a data record and transmitted to the API of the management entity for entry as a transaction in the blockchain.

In some embodiments, the practice app is configured to allow the doctor or a registered employee of the doctor's practice to assign a PC to a patient. The doctor or employee will create a PC data record for the digital twin of the doctor's practice. For example, key A of the corresponding PC is assigned to the identity of the corresponding patient. Further, fields are created, for example, for administration or logging of the administration of the PC to the patient. This assignment of patient and PC is logged in a data record and sent to the API of the management entity for entry as a transaction in the blockchain. In some embodiments, key A of the PC is transmitted to the API of the management entity in addition to the data record. Upon receipt of the key A, the API of the management entity will check, for example, in the digital twin of the management entity, whether there is indeed any PC with this key A. If there is not, the doctor or employee will receive an error message in the practice app. If there is a PC with the corresponding key A, i.e. if a PC with the corresponding key A is registered with the management entity and this PC has not yet been assigned to any other patient, the doctor's or employee's data record is forwarded to the blockchain for entry as a transaction. For example, in addition to information about changes made by the doctor or employee to the digital twin of the doctor's practice, the transaction comprises information about changes related to the PC in the digital twin of the management entity. For example, this information on the changes regarding the PC in the digital twin of the management entity is supplemented by the management entity in the transaction. For example, these changes regarding the PC in the digital twin of the management entity marks that this specific PC has now already been assigned to a patient once and cannot be assigned again.

In some embodiments, in the course of administration of the PC, the key A on the outer packaging of the PC is scanned, for example, by the patient. For example, the patient is prompted to scan the key A on the outer packaging of the PC by their electronic device running the corresponding application software or app. For example, scanning is performed using a camera on the patient's electronic device. For example, a QR code comprising the first key A is arranged on the outer packaging of the PC. For example, the patient scans the corresponding QR code on the outer packaging of the PC and sends a data record from their electronic device to the API of the management entity with information about the scanning of the outer packaging. For example, the data record comprises a timestamp, comprising, for example, the current date and time. Thus, the time of scanning the key A can be documented in the data record of the PC of the digital twin of the doctor's practice. If the logging procedure for the administration of the PC for the PC uniquely identifiable with the key A has already been run once, the corresponding patient has had their rights to the data record of the corresponding PC revoked and they no longer have any rights to write to this data record of the PC or to cause data to be written to this data record. The corresponding data record is forwarded by the API of the management entity to the blockchain for registration as a transaction.

In some embodiments, the key B on the container of the PC is scanned in the course of administration of the PC, for example by the patient. For example, the patient is prompted to scan the key B of the PC container by their electronic device running the corresponding application software or app. For example, scanning is performed using a camera on the patient's electronic device. For example, a QR code comprising the first key B is arranged on the container of the PC. For example, the patient opens the outer packaging of the PC and removes the container. For example, the patient scans the corresponding QR code on the PC container and generates a data record documenting the scanning of the key B on the container with a time stamp. For example, the data record comprises a timestamp. The timestamp comprises, for example, the current date and the current time.

For example, the data record comprises the previously scanned key A and the currently scanned key B. The data record is sent from the patient's electronic device to the API of the management entity that verifies that a key B associated with the PC with the key A in the management entity digital twin matches the key scanned from the PC's container. This makes it possible to effectively exclude the possibility of the outer packaging being mixed up or to exclude the possibility of the container being an unauthorised unpackaged container. If this review is successful, the data record will be forwarded to the blockchain with the timestamp of the scan of key B for registration as a transaction.

In some embodiments, a video of the administration is created in the course of administering the PC and transmitted for validation. For example, scanning key B or the QR code comprising the corresponding key B in the patient app may start a time window for administration of the PC. This administration is to be documented using a video. For example, a video is recorded within the time window documenting the administration of the PC. This video is encrypted and transmitted, for example to the doctor, for validation.

For example, the patient generates a data record upon completion of the video capture to transmit the video to the doctor. The video is encrypted using a cryptographic key for this purpose. For example, a key to decrypt the encrypted video is written to the digital twin of the doctor's practice and only accessible to the attending physician or employees of the doctor's practice who have been approved by the doctor. For example, the key is assigned to the PC. For example, the key is written to the PC data record in the digital twin of the doctor's practice. For example, the data record containing information on the above changes and the encrypted video are transmitted to the API of the management entity. The encrypted video is stored by the management entity in a memory, such as an IPFS memory. For example, access to the corresponding memory is restricted, i.e., the memory is an access-restricted memory. For example, the memory, such as IPFS memory, is associated with the blockchain. The data record is forwarded by the management entity to the blockchain for registration as a transaction. In another transaction, the API of the management entity documents a revocation of the patient's access rights to the PC, so that the patient can make small further changes with regard to the PC.

IPFS memory is a memory based on the "Inter Planetary File System" (IPFS). The IPFS is a protocol and namesake network that provides a content-addressable, peer-to-peer method for storing and sharing hypermedia in a distributed file system.

In some embodiments, the doctor calls up the video using the practice app to validate the administration of the PC. For example, the doctor queries the PC data record from the blockchain via the API of the management entity, comprising all data related to the administration of the PC. Using the private cryptographic key assigned to their identity, the doctor can prove their authorisation to decrypt the corresponding data. Of the PC data record, for example, a reference to the encrypted video in the access-restricted memory, such as one of the encrypted first data record via a network for storage in a storage system memory, is comprised. This video is provided to the doctor by the API of the management entity, decrypted on the doctor's electronic device, and displayed to the doctor for validation.

In some embodiments, the doctor views and validates the video or the administration of the PC documented in the video. The doctor will then transmit the validation result. For example, the doctor generates a data record that writes the result of the validation to the data record de PC of the digital twin of the doctor's practice or initiates a corresponding letter and transmits this data record with the result of the validation to the API of the management entity for forwarding to the blockchain for entry as a transaction.

In some embodiments, management of the data records provided for entry as a transaction on the blockchain is controlled by one or several smart contracts.

A smart contract is a computer protocol that maps a contract and/or procedural rules or verifies compliance with them.

Embodiments relate to a computer-implemented method for monitoring administration of a substance composition to a patient using a first computer system for compliance monitoring of the patient. The method comprises:

Recording administration of the substance composition using a camera of the first computer system, Creating an encrypted first data record comprising administration-related data using a first cryptographic key; in this, the administration-related data comprises the recording of the administration, Sending the encrypted first data record via a network for storage in a memory system, Transmitting a first data record identifier of the encrypted first data record and a first validator identifier of a first entity responsible for validating the encrypted first data record via the network for storage in a first registry entry of a registration database associated with the storage system, in which registry entries of the registration database are entries that each register an encrypted first data record stored in the storage system and associate it with an entity responsible for validating it.

The substance composition may in particular be a pharmaceutical substance composition (PC). The first computer system may be a patient electronic device for data processing, in particular a mobile electronic device.

In some embodiments, the encrypted first data record is stored with an intermediary server of a management entity. In some embodiments, the storage system is provided by the management entity. In some embodiments, the storage system is provided independently of the management entity The storage system may comprise, for example, an IPFS memory. For example, the storage system may be associated with a blockchain.

In some embodiments, storage in the first registry entry of the registration database takes place under with the management entity or its server as an intermediary.

The first entity responsible for validating the encrypted first data record is an AP or an institution, such as a doctor's practice, hospital, pharmacy, comprising one or several APs. For example, the first validator identifier is an identifier or digital identity of the AP.

Storing the encrypted first data record in a storage system, in particular in a non-public, for example access restricted, storage system, ensures that the data of the first data record remain secure in future, even if the encryption of the first data record was to lose its security. If the security of the encryption of the first data record is no longer sufficient, the encrypted data record can be decrypted and re-encrypted using a more secure encryption method. The data record with the now-insecure encryption can be replaced by the data record with the more secure encryption in the storage system. In contrast, entries in a blockchain, for example, cannot be replaced. If an encrypted data record is entered into a registration database in the form of a blockchain, there is a risk that it may be decrypted at some point in future. For example, if only one cryptographic key is entered into the blockchain to decrypt the first data record in encrypted form, the corresponding first data record in the storage system may be re-encrypted using a new cryptographic key and the previous version of the record may be replaced with the new version of the record in the storage system. The new cryptographic key may be stored in the registration database in encrypted form in turn, for example using a more secure encryption method. Even if the previous cryptographic key from the blockchain should fall into unauthorised hands, the security of the first data record can still be ensured in this way.

In some embodiments, the registration database is a blockchain and the first registry entry is stored as a transaction in the blockchain.

For example, the blockchain is a public blockchain with entries or transactions that are publicly accessible. In some embodiments, user data are only added to the transactions of the blockchain in encrypted form and/or only anonymised user data, such as identifiers in the form of synonyms, are added in an unencrypted form.

In some embodiments, the validator identifier is a destination address of the transaction associated with the first entity. For example, the destination address is an address derived from a public cryptographic key of the first entity.

In some embodiments, storage takes place as a transaction in the blockchain mediated by the management entity or its server. In some embodiments, an originating address of the transaction is an address associated with the management entity. For example, the source address is an address derived from a public cryptographic key of the management entity.

In some embodiments, the storage system is an access-restricted storage system. An access-restricted storage system is understood to be a non-public storage system for which a read authorisation must be proven in order to read stored data. A corresponding read authorisation can be proven, for example, using an authorisation certificate and/or a cryptographic key, for example, a symmetric cryptographic key or a private cryptographic key of an asymmetric key pair.

In some embodiments, the method further comprises sending a patient identifier of the patient and/or an identifier of the substance composition. For example, the patient identifier and/or the substance composition identifier allow the transmitted data to be associated with a patient and/or a substance composition for which an administration is documented. In some embodiments, the administration-related data comprises the patient identifier and/or the substance composition identifier.

In some embodiments, the first cryptographic key is a first public cryptographic key of a first asymmetric cryptographic key pair associated with the first entity. Thus, the encrypted first data record can only be decrypted using the associated first private cryptographic key of the first asymmetric cryptographic key pair of the first entity or the AP.

In some embodiments, the first cryptographic key is a first symmetric key. The method further comprises:
Encrypting the first symmetric key using the first public cryptographic key,
Sending the encrypted first symmetric key via the network for storage in the first registry entry of the registration database.

In some embodiments, the first cryptographic key is provided in encrypted form via the registration database, such as a blockchain. The first private cryptographic key associated with the first public cryptographic key is required to decrypt the first symmetric key. Thus, for example, the first entity or AP in possession of the first private cryptographic key is enabled to decrypt the symmetric key and thus the first data record. Use of symmetric encryption also has the advantage that symmetric encryption is faster than asymmetric encryption for the same available computing power. This can be of particular advantage for the efficiency of the method when dealing with large amounts of data, such as captured videos.

In some embodiments, the method further comprises: Generation of the first symmetric cryptographic key. For example, the first symmetric cryptographic key is generated by the patient on the first computer system.

In some embodiments, the substance composition comprises one or several pharmaceutical active substances. In some embodiments, the substance composition comprises one or several marker substances, preferably two or several different marker substances. In some embodiments, the different marker substances comprise polyethylene glycols having different molecular weights.

In some embodiments, the recording further comprises at least one of the following actions: Showing a face of the patient, opening an outer packaging comprising a container with the substance composition, removing the container with the substance composition from the outer packaging, opening the container, dispensing the substance composition from the container, showing the container completely or at least partially emptied after dispensing, showing the oral cavity of the patient after administration of the substance composition, showing an injection site on the patient after administration of the substance composition.

In some embodiments, the method further comprises: Scanning a first code on the outer packaging with the container with the substance composition. In some embodiments, the container is a blister pack comprising a plurality of compositions of matter, each substance composition having an individual first code associated therewith. For example, the first code comprises the key A.

In some embodiments, the method further comprises: Scanning a second code on the container containing the substance composition. For example, the second code comprises the key B. In some embodiments, the second code or key B is associated with the first code or key A, respectively.

The corresponding assignment is stored, for example, at the management entity, so that whether the correct container is in the outer packaging or whether the outer packaging present is the outer packaging belonging to the container can be checked based on the two scanned codes.

In some embodiments, creating the encrypted first data record, sending the encrypted first data record, and/or sending the first data record identifier and the first validator identifier are automatically initiated upon a completion of recording the administration by the first computer system. The automatic start may be triggered, for example, by completion of the recording of the administration or receipt of a user confirmation regarding the completion of the administration.

In some embodiments, the administration-related data comprises a timestamp. For example, the timestamp comprises the date and time.

In some embodiments, the method further comprises displaying an administration prompt using a display device of the first computer system. The display device may be, for example, a display of the first computer system.

In some embodiments, the method further comprises displaying a timer using the display device of the first computer system, in which the timer indicates an expiration of a predefined maximum time interval for administration of the substance composition.

In some embodiments, administration of the substance composition is an oral administration. In some embodiments, the substance composition is provided in the form of a capsule or a tablet.

In some embodiments, administration of the substance composition is a parenteral administration. In some embodiments, the substance composition is provided in the form of an injection kit.

In some embodiments, the first electronic computer system is a mobile portable telecommunication device.

In some embodiments, the method further comprises validating the encrypted first data record by the first entity responsible for validating the encrypted first data record using a second computer system for compliance control purposes. The method further comprises:
Receiving the first registry entry stored in the registration database associated with the first entity via the network,
Identifying the encrypted first data record using the first data record identifier provided by the first registry entry,
Receiving the encrypted first data record stored in the storage system via the network,
Decrypting the encrypted first data record,
Reviewing the administration-related data of the decrypted first data record to determine whether the administration-related data document proper administration of the substance composition in accordance with one or several administration instructions.

The second computer system is a computer system of the AP, for example, a doctor or a doctor's practice.

In some embodiments, the first encrypted data record is decrypted using a first private cryptographic key of the first asymmetric cryptographic key pair.

In some embodiments, the method further comprises:
Decrypting the first symmetric key comprised by the first registry entry encrypted with the first public cryptographic key using the first private cryptographic key,
Decrypting the encrypted first data record using the decrypted first symmetric cryptographic key.

In some embodiments, the method further comprises granting access rights to the encrypted first data record for one or several additional entities, with granting the access rights comprising the generation of a first key set comprising one or several encrypted copies of the first symmetric key, each comprising an individual encrypted copy of the first symmetric key for each of the additional entities, with generation of the individual encrypted copies of the first symmetric key each comprising the encryption of the first symmetric key decrypted using the first private key with a second public cryptographic key of a second asymmetric key pair associated with the corresponding additional entity.

For example, the additional entities may be additional APs, such as employees of a practice. Using the first set of keys, the symmetric key can be provided to a plurality of APs. Each copy of the symmetric key is assigned to an individual AP as a result of the encryption and can only be decrypted using the private cryptographic key of the corresponding AP.

In some embodiments, the method further comprises revoking one or several of the access rights of one of the additional entities to the first data record; this revocation comprises:
Receiving the first registry entry stored in the registration database associated with the first entity via the network,
Decrypting the first symmetric key comprised by the first registry entry encrypted with the first public cryptographic key using the first private cryptographic key,
Identifying the encrypted first data record using the data record identifier provided by the first registry entry,
Receiving the encrypted first data record stored in the storage system via the network,
Decrypting the encrypted first data record using the decrypted first symmetric cryptographic key,
Generating a third symmetric key,
Encrypting the decrypted first data record with the third symmetric key,
Sending the first data record encrypted with the third symmetric key via the network to replace the first data record encrypted with the first symmetric key in the storage system,
Generating a second key set comprising one or several encrypted copies of the third symmetric key, the second key set comprising one individual encrypted copy of the third symmetric key for each of the additional entities of the first key set except for the additional entities for which access rights are to be revoked, with the individual encrypted copies of the third symmetric key each being encrypted using the second public cryptographic key of the second asymmetric key pair associated with the corresponding additional entity.

The encrypted first data record can only be decrypted using the third symmetric key by replacing the first data record encrypted with the first symmetric key with the first data record encrypted with the third symmetric key. This ensures that an additional entity can effectively be denied access to the first data record. Even if the additional entity is still in possession of the first symmetric key, it is no longer able to decrypt the corresponding re-encrypted record as a result of the re-encryption of the first data record with the third symmetric key.

In some embodiments, revoking the access right further comprises replacing the first set of keys with the second set of keys.

In some embodiments, the administration instructions comprise one or several of the following instructions: Administration of the correct substance composition, administration to the correct patient, completeness of the administration, correct mode of administration of the substance composition, initiation of the administration within a predefined time window, execution of the administration within a predefined maximum time interval, execution of individual administration steps within predefined subintervals of the maximum time interval.

In some embodiments, a trained machine learning module is used to review the administration-related data; in this, reviewing by the trained machine learning module comprises:
Deploying the trained machine learning module,
Entering the decrypted first data record as input data to the trained machine learning module,
Receiving a test result as output data from the trained machine learning module in response to inputting the input data,
Issuing a warning and request for a manual review if the test result comprises indications of improper administration in deviation from one or several of the administration instructions.

Use of a trained machine learning module permits automated validation or at least automated validation support. For example, the machine learning module is configured to recognise the patient using a face recognition algorithm. Here, for example, it can be checked whether there is a sufficient match between a face of a person to be seen on the image and a stored photograph of the patient, to which the patient identifier is assigned, that the person to be seen on the image can be identified as the patient.

A machine learning module is an algorithm configured for machine learning. Machine learning refers to generation of knowledge from experience performed by a computer system: A computer system learns by example and can generalise after completing a learning phase when it is trained. For this purpose, an algorithm builds a statistical model based on training data in the course of machine learning. The static model is based on recognised patterns and regularities in the training data. Thus, the trained machine learning module is configured to evaluate unknown data in the course of a learning transfer. For example, the machine learning module comprises an artificial neural network. For example, the artificial neural network is an artificial neural network for deep learning. Deep Learning refers to a machine learning method using an artificial neural network with numerous intermediate layers between input layers.

In some embodiments, providing the trained machine learning module comprises training an untrained machine learning module; in this, the training comprises:
Providing a plurality of training data records, each of the training data records comprising respective administration-related training data and respective training test results associated with the administration-related training data, the training test results each indicating whether the corresponding administration-related training data document proper administration of a substance composition in accordance with one or several administration specifications or whether there is evidence of improper administration in deviation from one or several of the administration specifications,
For each of the training data records:
Entering the administration-related training data of the corresponding training data record as input data to the machine learning module,
Adjusting parameters of the machine learning module until an output of the machine learning module in response to the input of the corresponding input data provides output data that are a match for the training test result of the corresponding training data record that undercuts a predefined threshold.

Thus, effective training of the machine learning module may be enabled such that the trained machine learning module is configured to provide automated validation or at least automated support for validation.

In some embodiments, the method further comprises confirming the administration-related data:

Generating an encrypted second data record comprising an administration confirmation using a second cryptographic key upon successful review of the decrypted first data record, the review being successful if it indicates that the administration-related data document proper administration of the substance composition in accordance with one or several of the following, Sending the encrypted second data record via a network for storage in the storage system, Sending a second data record identifier of the encrypted second data record and the first validator identifier via the network for storage in a second registry entry in the registration database.

In some embodiments, the second data record and/or the second registry are stored with the management entity as an intermediary. For example, the second computer system is a computer system of an AP.

In some embodiments, the method further comprises sending the patient identifier of the patient and/or an identifier of the substance composition. In some embodiments, the administration confirmation comprises the patient identifier and/or the substance composition identifier.

In some embodiments, the second cryptographic key is the first public cryptographic key.

In some embodiments, the second cryptographic key is a second symmetric key, the method further comprising:

Encrypting the second symmetric key using the first public cryptographic key,

Sending the encrypted second symmetric key via the network for storage in the second registry entry of the registration database.

In some embodiments, the method further comprises: Generating the second symmetric cryptographic key. For example, the second computer system generates the second symmetric cryptographic key.

In some embodiments, the method further comprises receiving a request to validate the encrypted first data record via the network in response to storing the first registry entry in the registration database. For example, the management entity may inform the second computer system of storage of the first registry entry or request validation of the encrypted first data record. For example, this may happen in response to receipt of the first registry entry by the management entity for storage in the storage system, in which the management entity identifies the first entity or the second computer system using the validator identifier. Alternatively, the management entity may repeatedly query the registration database for registry entries that comprise the first-entity validator identifier and/or comprise a timestamp that is more recent than a most recent query of the registration database.

In some embodiments, the method further comprises: repeatedly querying the registration database via the network for registry entries comprising the validator identifier of the first entity. Thus, the AP can use the queries to determine on its own whether there are any relevant registry entries.

In some embodiments, querying is limited in each case to registry entries that comprise a timestamp that is more recent than a most recent query of the registration database.

Embodiments further relate to a computer program configured to control the first computer system upon execution by a first processor of a first computer system to perform a method of monitoring an administration of a substance composition to a patient for compliance control of the patient:

Recording administration of the substance composition using a camera of the first computer system, Creating an encrypted first data record comprising administration-related data using a first cryptographic key; in this, the administration-related data comprises the recording of the administration, Sending the encrypted first data record via a network for storage in a memory system, Transmitting a first data record identifier of the encrypted first data record and a first validator identifier of a first entity responsible for validating the encrypted first data record via the network for storage in a first registry entry of a registration database associated with the storage system; in this, registry entries of the registration database are entries that each register an encrypted first data record stored in the storage system and associate it with an entity responsible for validating it.

This computer program is, for example, a patient app that is executed on a computer system of the patient, in particular a mobile portable telecommunications device, such as a smartphone.

Embodiments further relate to a computer program configured to control, upon execution by a second processor of a second computer system, the second computer system to execute a method for validating an encrypted first data record by a first entity responsible for validating the encrypted first data record for compliance control of a patient; in this, the encrypted first data record comprises administration-related data including a record of an administration of a substance composition to the patient, including:

Receiving a first registry entry stored in a registration database associated with a storage system via the network, the first registry entry comprising a first data record identifier of the encrypted first data record and a first validator identifier of the first entity; in this, registry entries of the registration database are entries each registering an encrypted first data record stored in the storage system and associating it with an entity responsible for validating it, Identifying the encrypted first data record using the first data record identifier provided by the first registry entry, Receiving the encrypted first data record stored in the storage system via the network, Decrypting the encrypted first data record, Reviewing the administration-related data of the decrypted first data record to determine whether the administration-related data document proper administration of the substance composition in accordance with one or several administration instructions.

This computer program is, for example, an app of the AP, such as a patient app, that runs on a computer system of the AP.

In some embodiments, the above computer programs are configured to perform any of the previously described embodiments of the method of monitoring the administration of a substance composition.

Embodiments further relate to a computer system for monitoring administration of a substance composition to a patient for compliance control of the patient, the computer system comprising a processor, a memory, a camera, and a communication interface for communicating via a network, the memory having stored therein first program instructions of a first computer program, the first program instructions configured to control the computer system upon execution by the processor:

Recording administration of the substance composition using a camera of the first computer system, Creating an encrypted first data record comprising administration-related data using a first cryptographic key; in this, the administration-related data comprise the recording of the administration, Sending the encrypted first data record via the network for storage in a memory system, Transmitting a first data record identifier of the encrypted first data record and a first validator identifier of a first entity responsible for validating the encrypted first data record via the network for storage in a first registry entry of a registration database associated with the storage system; in this, registry entries are entries in the registration database that each register an encrypted first data record stored in the storage system and associate it with an entity responsible for validating it.

This computer system is, for example, a patient's computer system, in particular a mobile portable telecommunications device, such as a smartphone.

Embodiments further relate to a computer system for validating an encrypted first data record by a first entity responsible for validating the encrypted first data record for compliance monitoring of a patient; in this, the first encrypted data record comprises administration-related data including a record of administration of a substance composition to the patient; in this, the computer system comprises a processor, a memory and a communication interface for communicating via a network, with second program instructions of a second computer program being stored in the memory, and the second program instructions being configured to control the computer system upon execution by the processor:

Receiving a first registry entry stored in a registration database associated with a storage system via the network, the first registry entry comprising a first data record identifier of the encrypted first data record and a first validator identifier of the first entity; in this, registry entries of the registration database are entries each registering an encrypted first data record stored in the storage system and associating it with an entity responsible for validating it, Identifying the encrypted first data record using the first data record identifier provided by the first registry entry, Receiving the encrypted first data record stored in the storage system via the network, Decrypting the encrypted first data record, Reviewing the administration-related data of the decrypted first data record to determine whether the administration-related data document proper administration of the substance composition in accordance with one or several administration instructions.

For example, this computer system is a computer system of the AP.

In some embodiments, the above computer systems are configured to perform any of the previously described embodiments of the method of monitoring the administration of a substance composition.

Embodiments further relate to a system comprising a storage system, a registration database associated with the storage system, a first computer system according to any one of the preceding embodiments, and a second computer system according to any one of the preceding embodiments.

In some embodiments, the system is configured to perform any of the previously described embodiments of the method of monitoring the administration of a substance composition.

The invention claimed is:

1. A method for using a pharmaceutical composition in endogenous marking of a urine sample, wherein the pharmaceutical composition contains no active substance but merely a combination of at least two marker substances and wherein the marker substances are polyethylene glycols with different molecular weights, characterized by the following steps:

Registering every individual dose of the pharmaceutical composition in its production and subsequent packaging in a blockchain, wherein all relevant actions of the parties involved in the process regarding this pharmaceutical composition are registered in the blockchain for seamless logging from production to intake of the pharmaceutical composition;

Marking of an outer packaging with a first digital code;

Scanning of the first digital code by a dispensing office;

Linking of patient data of a patient with data of an authorized person, wherein the blockchain links the units involved so that a coherent information chain results;

Starting an application software by the patient;

Scanning the first digital code by the application software;

Starting a video recording;

Presenting integrity of the outer packaging;

Taking a container with the pharmaceutical composition out of the outer packaging;

Scanning a second digital code on the container with the pharmaceutical composition;

Opening the container;

Taking the pharmaceutical composition out of the container;

Taking the pharmaceutical composition;

Termination of the video recording;

Transmission of the video recording to the authorized person and through the application software to the blockchain;

Validation of the documented intake by the authorized person.

2. The method according to claim 1, characterized in an inspection of the oral cavity that is performed after intake of the pharmaceutical composition.

3. The method according to claim 1, characterized in that the time of performing of the method is determined by the authorized person.

4. The method according to claim 3, characterized in that the patient receives an electronic message one day before the specified date for performing the method.

5. The method according to claim 1, characterized in that the scanning of the second code starts a time window.

6. The method according to claim 5, characterized in that the time window is up to 120 seconds.

7. The method according to claim 5, characterized in that the patient must make a new appointment with the authorized person if the time window is exceeded.

8. The method according to claim 1, characterized in that scanning of the first code activates an encrypted data transmission.

9. The method according to claim 1, characterized in that the electronic device is a mobile electronic device.

10. The method according to claim 1, characterized in that the pharmaceutical composition has the form of a capsule.

11. The method according to claim 1, characterized in that the pharmaceutical composition has the form of a tablet.

12. The method according to claim 1, characterized in that the pharmaceutical composition is administered parenterally.

13. An outer packaging with a container arranged in it with a pharmaceutical composition for use in the method according to claim 1, wherein the outer packaging is marked with a first digital code, wherein the outer packaging is designed so that several manipulation protection features apply during an opening process, wherein the container is marked with a second digital code, wherein the pharmaceutical composition does not contain any active substance but only a combination of at least two marker substances and wherein the marker substances are polyethylene glycols with different molecular weights.

14. A non-transitory computer readable medium comprising instructions stored thereon for performing the following steps of the method according to claim 1:
Scanning a first digital code on an outer packaging with a container arranged in it with a pharmaceutical composition, wherein the pharmaceutical composition does not contain any active substance but only a combination of at least two marker substances and wherein the marker substances are polyethylene glycols with different molecular weights;
Receiving of data from a blockchain, wherein all relevant actions of the parties in the process regarding this pharmaceutical composition are registered in the blockchain for seamless logging from production to intake of the pharmaceutical composition, wherein the blockchain links the units involved so that a coherent information chain results;
Permitting a video recording of:
presenting integrity of the packaging;
taking the container with the pharmaceutical composition out of the outer packaging;
scanning a second digital code located on the container with the pharmaceutical composition,
opening the container;
taking the pharmaceutical composition out of the container;
taking the pharmaceutical composition;
Transmitting the recorded video to the blockchain.

15. A mobile device containing a non-transitory computer readable medium, wherein said non-transitory computer readable medium comprises instructions stored thereon for performing the following steps of the method according to claim 1:
Scanning a first digital code on an outer packaging with a container arranged in it with a pharmaceutical composition, wherein the pharmaceutical composition does not contain any active substance but only a combination of at least two marker substances and wherein the marker substances are polyethylene glycols with different molecular weights;
Receiving of data from a blockchain, wherein all relevant actions of the parties in the process regarding this pharmaceutical composition are registered in the blockchain for seamless logging from production to intake of the pharmaceutical composition, wherein the blockchain links the units involved so that a coherent information chain results;
Permitting a video recording of:
presenting integrity of the packaging;
taking the container with the pharmaceutical composition out of the outer packaging;
scanning a second digital code located on the container with the pharmaceutical composition,
opening the container;
taking the pharmaceutical composition out of the container;
taking the pharmaceutical composition; and
Transmitting the recorded video to the blockchain.

* * * * *